US00PP19563P3

(12) United States Plant Patent
Zaiger et al.

(10) Patent No.: US PP19,563 P3
(45) Date of Patent: Dec. 9, 2008

(54) INTERSPECIFIC TREE NAMED 'CORAL-COT'

(50) Latin Name: *Prunus*
Varietal Denomination: Coral-Cot

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 151 days.

(21) Appl. No.: 11/656,023

(22) Filed: Jan. 22, 2007

(65) Prior Publication Data

US 2008/0184405 P1 Jul. 31, 2008

(51) Int. Cl.
*A01H 5/00* (2006.01)

(52) U.S. Cl. ..... Plt./180

(58) Field of Classification Search ..... Plt./180, Plt./186
See application file for complete search history.

*Primary Examiner*—Howard J Locker

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. A regular and productive bearer of large freestone fruit.
2. The interspecific tree being self-fruitful, producing fruit with its own pollen.
3. Producing fruit with very good flavor and eating quality.
4. Fruit having an attractive orange skin color.
5. Fruit having firm flesh with good storage and shelf life.
6. Vigorous, semi-spreading tree growth.

1 Drawing Sheet

Botanical classification: Interspecific *Prunus* species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific, apricot, plum and plumcots, which are known to us, and mentioned herein, are 'Tri-Gem' Apricot (U.S. Plant Pat. No. 6,755), 'Flaming Gold' Apricot (U.S. Plant Pat. No. 2,822), 'PA7005-8' Apricot (U.S. Plant Pat. No. 7,034), 'Modesto' Apricot (U.S. Plant Patent No. 2,543), 'King Cot' Apricot (non-patented), 'Moniqui' Apricot (non-patented), the interspecific 'Splash' (U.S. Plant Patent No. 14,583) and the proprietary parents '9Z38A', '160LH337' and '4G1180'.

ORIGIN OF THE VARIETY

The new and distinct variety of interspecific tree, [[*Prunus armeniaca*×((*Prunus salicina*×(*Prunus salicina*×*Prunus armeniaca*)×(*Prunus salicina*×*Prunus armeniaca*))]×*Prunus armeniaca*] was originated by us in our experimental orchard located near Modesto, Calif. as a first generation cross between proprietary lines of immediate parents with field identification numbers '9Z38A' and '160LH337'. The maternal parent (9Z38A) originated from crosses of the following parents, 'Tri-Gem' Apricot (U.S. Plant Pat. No. 6,755), 'Modesto' Apricot (U.S. Plant Pat. No. 2,543), 'Splash' Interspecific (U.S. Plant Pat. No. 14,583) crossed with the white flesh apricot 'Moniqui' (non-patented). The paternal proprietary parent (160LH337) originated from crosses between the following apricots, 'King' Apricot (non-patented), 'Flaming Gold' Apricot (U.S. Plant Pat. No. 2,822) and 'PA7005-8' Apricot (U.S. Plant Pat. No. 7,034). A large number of these first generation crosses were budded on older trees of 'Nemaguard' Rootstock (non-patented), to induce earlier fruit production. One budded seedling exhibited desirable fruit and tree growth characteristics and was selected in 2001 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree [[Apricot×((Plum×Plumcot)×Plumcot)]×Apricot] is of large size, vigorous, semi-spreading growth and a productive and regular bearer of large, orange flesh fruit with very good flavor and eating quality. The fruit is further characterized by having an attractive orange skin color, firm flesh, with good handling and shipping quality and being relatively uniform in size and maturity throughout the tree. In comparison to its maternal parent, (9Z38A) the new variety is larger in size, orange flesh compared to white flesh and is approximately 10 days earlier in maturity. In comparison to its paternal parent, (160LH337) the new variety has firmer flesh, has a darker orange, more attractive skin color and is self fertile having good production without a pollinator.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color.

Tree:

*Size.*—Large, usually pruned to 3 to 3.5 meters in height and width for economical harvesting of fruit.

*Vigor.*—Vigorous, growth of 1.5 to 2 meters in height the first growing season. Varies with fertility and type of soil, climatic conditions and cultural practices.

*Form.*—Semi-spreading, usually pruned to vase shape.

*Branching habit.*—Semi-spreading, crotch angle approximately 40°, increases with heavy crop load.

*Productivity.*—Productive, thinning and spacing of fruit desirable. Fruit set varies with climatic conditions during blooming period.

*Bearer.*—Regular, has set an adequate crop 3 consecutive years with no alternate bearing observed.

*Fertility.*—Self fertile.

*Density.*—Medium dense, usually pruned to vase shape to allow more sunlight to center of tree to enhance fruit color and health of fruit spurs.

*Hardiness.*—Tree grown in USDA Hardiness Zone 9. Hardy in all stone fruit growing areas of California. Winter chilling requirement of approximately 400 hours at or below 45° F.

Trunk:

*Size.*—Medium. Average circumference 45.7 cm at 25.4 cm above ground.

*Stocky.*—Medium stocky.

*Texture.*—Medium shaggy, increases with age of growth.

*Color.*—Varies from 7.5YR 3/4 to 10YR 3/2.

Branches:

*Size.*—Medium. Average circumference 16.5 cm at 1.2 meters above ground. Crotch angle approximately 40°, increases with heavy crop.

*Surface texture.*—New growth smooth. Mature growth medium rough, roughness increases with age.

*Lenticels.*—Average number 42 in 25.8 sq cm surface area of branch. Average length 3.7 mm. Average width 1.5 mm. Color varies from 10YR 7/8 to 2.5Y 8/8.

*Color.*—New growth varies from 5GY 4/6 to 10R 2/6, depending on exposure to sunlight. Old growth varies from 7.5YR 5/2 to 7.5YR 3/4, varies with age of growth.

Leaves:

*Size.*—Large. Average length 91.0 mm. Average width 68.5 mm.

*Form.*—Ovate.

*Apex.*—Acuminate.

*Base.*—Obtuse.

*Margin.*—Doubly serrate.

*Thickness.*—Medium.

*Surface texture.*—Upper surface relatively smooth, very slightly indented over midrib and leaf veins, glabrous. Lower surface relatively smooth, except for small ridges caused by midrib and pinnate venation, glabrous.

*Petiole.*—Average length 37.5 mm. Average width 1.7 mm. Longitudinally grooved. Surface glabrous. Color varies from 5R 3/6 to 2.5GY 6/6, varies with exposure to sunlight.

*Glands.*—Type — globose. Size — small. Average length 0.7 mm. Average width 0.6 mm. Number — average 2, varies from 0 to 3. Located primarily on upper portion of petiole, base of leaf blade. Color varies from 5GY 5/6 to 7.5R 3/6.

*Color.*—Upper surface varies from 5GY 3/6 to 7.5GY 3/4. Lower surface varies from 5GY 5/4 to 5GY 4/4. Midvein color varies from 5GY 8/4 to 5GY 7/6.

Flower buds:

*Size.*—Small to medium. Average length 12.6 mm. Average diameter 8.5 mm.

*Hardiness.*—Hardy with respect to California winters.

*Form.*—Conical, becoming slightly elongated just before opening.

*Pedicel.*—Short. Average length 2.0 mm. Average width 1.9 mm. Color varies from 2.5GY 7/6 to 2.5GY 6/6.

*Color.*—Varies from 7.5RP 9/2 to 10RP 8/6.

*Number of buds per spur.*—Varies from 2 to 6, varies with age of spur.

Flowers:

*Size.*—Medium to large. Average height 19.3 mm. Average diameter 27.5 mm.

*Petals.*—Number — 5, alternately arranged to sepals. Size — average length 14.1 mm. Average width 14.3 mm. Form — orbicular. Margin — sinuate. Color varies from 7.5RP 9/2 to 10RP 9/2, fades with age of flower.

*Sepals.*—Number — 5, alternately arranged to petals. Size — medium. Average length 6.2 mm. Average width 5.7 mm. Shape — ovate, apex rounded. Margin — entire. Both upper and lower surfaces glabrous. Color — upper surface varies from 2.5R 3/8 to 5R 2/6. Lower surface varies from 2.5R 2/8 to 5R 2/8.

*Stamens.*—Average number per flower 29. Average filament length 12.7 mm. Filament color N 9.5/ (white). Anther color varies from 5Y 8/10 to 7.5Y 8.5/10.

*Pollen.*—Self fertile — fruit set while under a bag. Color varies from 5Y 8/10 to 5Y 7/8.

*Pistil.*—Normally one. Surface pubescent. Average length 12.8 mm. Position of stigma average of 1.9 mm below anthers. Color varies from 10Y 8/4 to 10Y 7/6.

*Fragrance.*—Slight.

*Blooming period.*—Date of First Bloom Feb. 12, 2005. Date of Petal Fall Feb. 20, 2005, varies sightly with climatic conditions.

*Color.*—Varies from 5RP 9/2 to N 9.5/ (white), fades with age of flower.

*Number flowers per flower bud.*—Usually one, varies from 1 to 2.

*Pedicel.*—Average length 2.5 mm. Average width 2.3 mm. Color varies from 10Y 8.5/4 to 10Y 8/6.

Fruit:

*Maturity when described.*—Firm ripe.

*Date of first picking.*—Jun. 6, 2005.

*Date of last picking.*—Jun. 11, 2005, varies slightly with climatic conditions.

*Size.*—Large. Average diameter axially 63.9 mm. Average transversely in suture plane 62.5 mm. Average across suture plane 59.0 mm. Average weight 133.5 grams, average weight varies slightly with fertility of the soil, amount of thinning and climatic conditions.

*Form.*—Elongated, slightly flattened inward toward suture plane.

*Suture.*—Distinct. Extends from base to apex.

*Ventral surface.*—Lipped, well sealed.

*Apex.*—Slightly retuse.

*Base.*—Flat to slightly retuse.

*Cavity.*—Rounded to slightly elongated in suture plane. Average depth 5.1 mm. Average diameter 11.3 mm.

Stem:

*Size.*—Small to medium. Average length 7.1 mm. Average diameter 3.4 mm.

*Color.*—Varies from 2.5GY 5/8 to 5GY 5/8.

Flesh:

*Ripens.*—Evenly.

*Texture.*—Firm on outer surface near skin, toward pit cavity smooth and juicy.

*Fibers.*—Few, very small, tender.

*Firmness.*—Firm, firmer than most commercial apricots.

*Aroma.*—Slight.

*Amydgalin.*—Slight.

*Eating quality.*—Very good.

*Flavor.*—Very good, with good balance between acid and sugar.

*Juice.*—Moderate amount, enhances flavor.

*Brix.*—Average Brix 17.8°, varies slightly with amount of fruit per tree and climatic conditions.

*Color.*—Orange, varies from 5YR 7/10 to 5YR 7/12. Pit cavity varies from 6.25YR 7/12 to 6.25YR 6/12.

Skin:

*Thickness.*—Medium.

*Surface.*—Nearly smooth, very slightly waffled.

*Down.*—Light amount, very short in length.

*Tendency to crack.*—Usually none, one season had small amount of blossom end cracks.

*Color.*—Varies from 7.5YR 7/14 to 5YR 6/12, where exposed to sunlight a slight blush develops which varies from 10R 4/8 to 10R 3/10.

*Tenacity.*—Tenacious to flesh.

*Astringency.*—None.

Stone:

*Type.*—Freestone.

*Size.*—Large. Average length 32.6 mm. Average width 22.9 mm. Average thickness 12.3 mm.

*Form.*—Obovoid.

*Base.*—Usually flat, varies on some stones from flat to slightly rounded.

*Apex.*—Slight point. Average length 0.3 mm.

*Surface.*—Slightly pitted throughout. Pits vary from round to elongated.

*Sides.*—Unequal, one side extending further from suture plane.

*Ridges.*—Small, narrow ridge next to groove on each side of suture, extends from base to apex.

*Tendency to split.*—None.

*Color.*—Varies from 10YR 4/4 to 10YR 3/4.

Kernal:

*Form.*—Ovoid.

*Viability.*—Viable, complete embryo development.

*Size.*—Large. Average length 20.9 mm. Average width 13.3 mm. Average depth 8.2 mm.

*Skin.*—Color varies from 2.5Y 8.5/4 to 5Y 8.5/2.

Use: Dessert. Market — local and long distance.

Keeping quality: Good, held firm in cold storage 2 weeks at 38° to 42° F. without shriveling, internal breakdown of flesh or appreciable loss of eating quality.

Shipping quality: Good, showed minimal skin scarring or bruising of flesh during picking, packing and shipping trials.

Plant/fruit disease resistance susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct interspecific tree, substantially as illustrated and described, characterized by its large size, vigorous, semi-spreading growth, and being a productive and regular bearer of large fruit with an attractive orange skin color, with very good flavor and eating quality; the fruit is further characterized by having firm flesh, good handling and shipping quality and in comparison to its maternal parent, the new variety has orange flesh fruit, compared to white flesh and the fruit is approximately 10 days earlier in maturity.

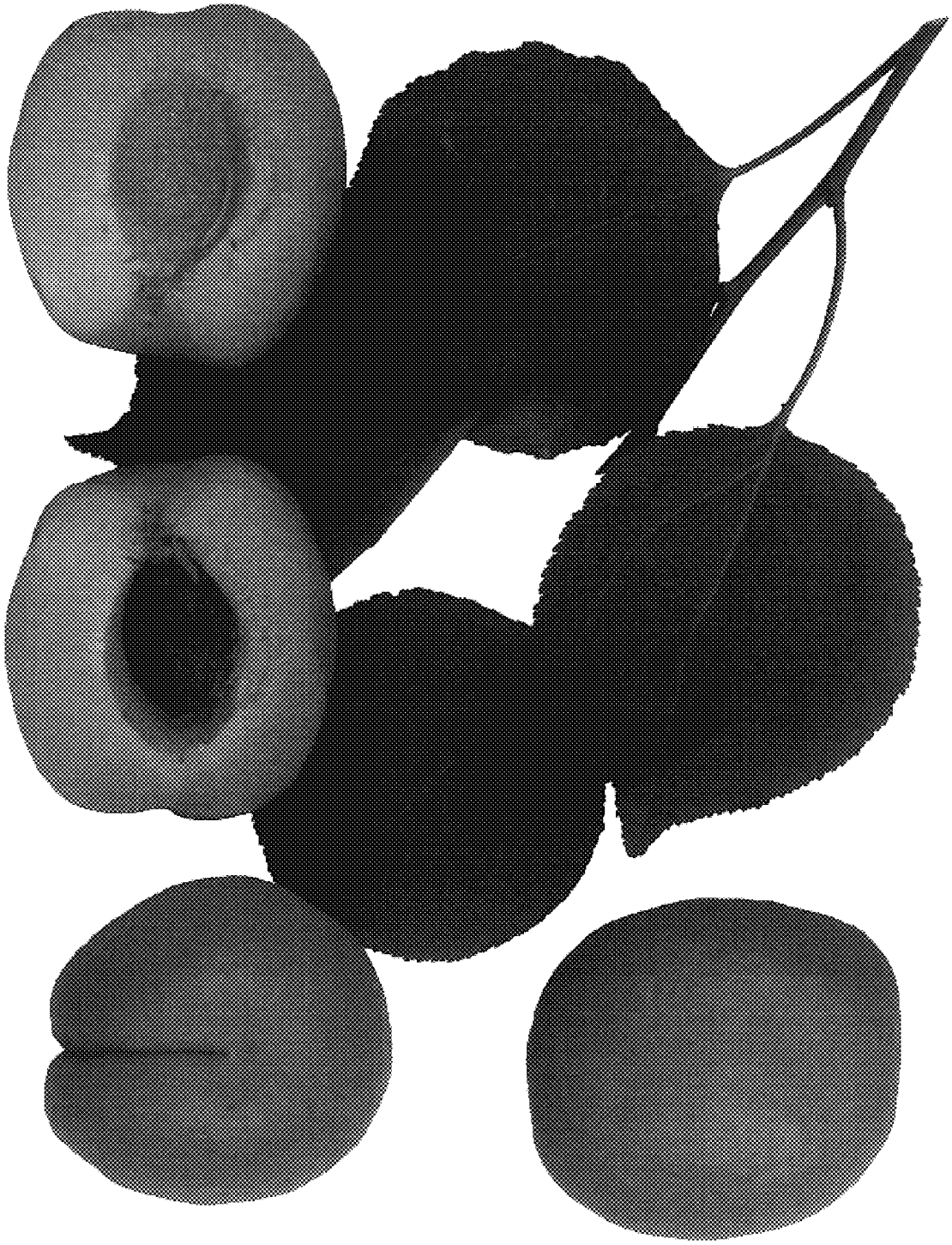

* * * * *